United States Patent [19]

Butler et al.

[11] Patent Number: 4,489,214

[45] Date of Patent: Dec. 18, 1984

[54] PRODUCTION OF ORTHO-SUPPRESSED DIALKYL BENZENES

[75] Inventors: James R. Butler; Debra L. Kendall; Cleve H. Forward; James M. Watson; Gary D. Branum, all of Big Spring, Tex.

[73] Assignee: Cosden Technology, Inc., Dallas, Tex.

[21] Appl. No.: 353,448

[22] Filed: Mar. 1, 1982

[51] Int. Cl.$^3$ .................................................. C07C 2/68
[52] U.S. Cl. ..................................................... 585/467
[58] Field of Search ......................................... 585/467

[56] References Cited

U.S. PATENT DOCUMENTS

| | | | |
|---|---|---|---|
| 4,140,319 | 8/1978 | Kaeding | 585/467 |
| 4,238,318 | 12/1980 | Kouwenhoven et al. | 208/137 |
| 4,283,306 | 8/1981 | Herkes | 585/467 |

FOREIGN PATENT DOCUMENTS 0021475  1/1981  European Pat. Off. .

OTHER PUBLICATIONS

Olson et al., *Journal of Catalysis*, 61, 390–396, (1980).

*Primary Examiner*—Curtis R. Davis
*Attorney, Agent, or Firm*—John K. Abokhair

[57] ABSTRACT

A process for suppressing production of ortho isomers during catalytic alkylation of monoalkylbenzenes which comprises contacting the aromatic substrate with an alkylating agent in the presence of a crystalline silica polymorph silicalite catalyst material.

13 Claims, No Drawings

4,489,214

PRODUCTION OF ORTHO-SUPPRESSED DIALKYL BENZENES

TECHNICAL FIELD

This invention relates to a process for producing dialkyl substituted benzene isomer mixtures in which the amount of ortho isomer present in the product mix is substantially less than a thermodynamic equilibrium amount. In another aspect this invention relates to the production of ortho-poor isomer mixtures of dialkyl substituted benzenes through use of an intrinsically ortho-suppressive crystalline silica catalyst of the silicalite type. A still further aspect of this invention relates to a process for producing ethyl-toluene using a crystalline silica polymorph catalyst of the silicalite type wherein the ethyltoluene isomer mixture has substantially less ortho isomer than would be contained in a thermodynamic equilibrium isomer mix.

BACKGROUND ART

The presence of ortho isomers of dialkyl substituted benzenes in isomer mixes of these compounds is known to be undesirable. Ortho-isomers of dialkyl substituted benzenes are to be avoided because upon dehydrogenation of such materials to form vinyl aromatic products ring closures can occur and form bicyclo derivatives such as indenes and indanes. The latter compounds both adversely affect the properties of the desired vinyl aromatic products and reduce the recoverable amount of such products from the dialkyl substituted benzene isomer mix. If such compounds are formed separation by expensive superfractionation processes prior to dehydrogenation is required. However, thermodynamics predict that a substantial amount of ortho isomer will be present in a dialkyl substituted benzene product mix of para, meta, and ortho isomers. For example, a thermodynamic equilibrium for an isomer mix of ethyltoluene is approximately 31.5% para, 50.2% meta and 18.3% ortho at temperatures effective for vapor phase alkylation. Since the isomer mixes are only difficulty separated into para, meta, and ortho fractions, processes which produce a reduced amount of ortho in the original isomer mix are highly desirable.

Recently aluminosilicate type zeolite catalysts, including those known as "ZSM-5" type catalysts materials have been reported to be suitable for hydrocarbon conversion processes and, in particular, for the alkylation of aromatic substrates. One problem with these types of catalysts, however, is that they are subject to rapid deactivation in the presence of even small amounts of water. Thus, when using such catalysts, it is sometimes necessary to reduce the moisture content of feedstock materials prior to their introduction into a conversion zone. Furthermore to the extent such materials have been disclosed as being useful in isomer selective processes (such as the para-selective processes disclosed in U.S. Pat. No. 4,086,287, 4,117,024, 4,117,026, 4,127,616, 4,128,592 and the ortho suppressive process disclosed in U.S. Pat. No. 4,094,921) these aluminosilicates zeolites must be modified either chemically or by prior steam treatment or coking in order to be useful as isomer selective catalyst materials. Thus, a process for alkylating aromatic substrates to obtain dialkyl aromatics whereby production of the ortho isomer is suppressed by employing catalyst materials which do not require special modification and have a high level of conversion would be desirable.

SUMMARY OF THE INVENTION

It has now been discovered that isomer mixtures of dialkyl substituted benzenes having substantially reduced amounts of ortho isomer can be produced by contacting toluene, ethylbenzene or mixtures thereof with an alkylating agent under alkylation conditions in the presence of a crystalline silica polymorph silicalite catalyst. The silicalite catalyst materials are not chemically or thermally modified in any special manner and are used substantially as prepared in accordance with the disclosures of U.S. Pat. No. 4,061,724, the entire disclosure of which is incorporated by reference. We have discovered that these unique catalysts intrinsically provide isomer selectivity which favors production of the para and meta isomers over the ortho isomer as compared to the expected thermodynamic equilibrium (31.5/50.2/18.3) isomer mix.

In general, monoalkyl substituted benzenes such as toluene and ethylbenzene can be alkylated by reacting same with an alkylating agent, such as ethylene for example, in the presence of a silicalite catalyst material under reaction conditions comprising reaction zone inlet temperatures of from about 350° to about 500° C. Pressures of from about atmospheric at about 25 atmospheres, weight hourly space velocities of aromatic feedstocks of from about 10 to about 200 and aromatic: alkene molar feed ratios of from about 2:1 to about 20:1 can also be employed during alkylation.

Because silicalite materials are steam stable, steam cofeed can be employed during the reaction, and, in many instances, can actually benefit the process by reducing production of unwanted products and increasing stability and selectivity of the catalysts. For details see our copending application Ser. No. 06/255,882, now abandoned. Steam cofeed, that is, the introduction of a specified amount of water to the reaction zone during alkylation should not be confused with steam pretreatment or modification of the catalyst materials prior to their use in the reaction zone.

The process of the present invention will provide a suppression of the production of ortho isomer so that the dialkyl benzene isomer mix produced will have substantially less ortho isomer than that expected from thermodynamic prediction. For example, when producing ethyltoluene, substantially less than the 18% ortho isomer which would be thermodynamically expected is produced. The process can be used to produce isomer mixes having concentrations of ortho isomer of less than 5% and in some cases as low as 0.02% by weight of the product.

DETAILED DESCRIPTION

The process of the present invention comprises suppressing production of ortho isomers during catalytic alkylation of toluene or ethylbenzene by feeding the aromatic substrate and alkylating agent to a conversion zone containing a crystalline silica polymorph silicalite type catalyst wherein the reactants are allowed to contact the catalyst under controlled conversion temperatures pressures and residence times. The process can be carried out using a variety of processing equipment, including a reactor vessel which defines an alkylation zone containing silicalite catalyst material. Either singular or multiple catalyst beds can be employed in the reaction zone. The hydrocarbon reactants, which preferably include toluene or ethylbenzene as aromatic substrates and ethylene or methanol as alkylating agents, can be admixed and preheated prior to introduction into the reaction zone where they contact the catalyst beds under reaction conditions further specified hereinbelow. The mole ratio of aromatic substrate to alkylating agent will be controlled in accordance with the desired reaction product. If desired, steam can be admixed with the reactants just prior to introduction to the reaction zone. After a controlled residence time within the reaction zone, the converted hydrocarbon charge passes out of the reactor where the desired products are collected by cooling or other standard recovery techniques.

Reaction conditions should include inlet temperatures in a range of from about 350° C. to about 500° C. with a range of about 410° C. to about 475° C. being especially preferred. Reactant mole feed ratios will generally be from about 2:1 to about 20:1, aromatic:alkylating agent. Pressures can vary from atmospheric to 25 atmospheres, with pressures in the range of from about 10 to about 15 atmospheres being preferred. Weight hourly space velocity of aromatic substrates are preferably from about 50 to about 200 with a range of from about 75 to about 150 being particularly preferred. Higher weight hourly space velocities, resulting in greater kinetic control of the process, may also be useful. When steam cofeed is employed, a range of from about 20,000 to about 60,000 ppm based on the aromatic feed is preferred with 40,000 ppm being especially preferred.

The catalyst materials employed by the process of the subject invention are true crystalline silica materials as opposed to a zeolitic material, which, be definition, is a silicate of aluminum and either sodium or calcium, or both, which demonstrates ion exchange capacity. The crystalline silica materials used as catalysts in the present invention are silica polymorphs whose structure has been designated as "silicalite". These materials, in contrast to aluminosilicate zeolites, demonstrates no appreciable ion exchange properties since the $AlO^-_4$ tetrahedra do not comprise a portion of the crystalline silica framework. Aluminum may be present in these silicalite catalyst materials, however, its presence is a result of impurities in the silica source used to prepare the material and silicalite containing such alumina or other metal oxide impurities can in no sense be considered to be a metalosilicate. Further description and methods for preparing silicalite type catalysts are set forth in the above mentioned U.S. Pat. No. 4,061,724.

In addition to the physical and chemical distinctions between crystalline silica polymorph silicalite type catalysts and aluminosilicate zeolites, several functional distinctions are also apparent as regards the use of these materials as alkylation catalysts. For example, ZSM-5 type aluminosilicalite zeolites currently used in alkylation aromatic processes are reported to rapidly lose catalytic activity in the presence of even minor amounts of water. As noted hereinabove, the crystalline silica polymorph silicalite materials of the present invention are useful as hydrocarbon conversion catalysts even in the presence of steam and, in some instances, alkylation processes can obtain enhanced performance through the use of steam cofeed.

While the precise mechanism by which the ortho isomer is suppressed during alkylation reactions employing the silicalite catalyst materials is not known this ability is apparently due to the innate nature of these particular type of catalyst materials and not to any modification treatment or coking which might occur during processing. This is evidenced by the fact that silicalite catalysts have demonstrated the ability to suppress ortho isomer production during preparation of ethyltoluene or both relatively young (0-10 hours) and old (over 300 hours) catalyst age. Further, the ortho suppression can be observed even in the presence of steam cofeed which ordinarily is considered to retard coking of the interior pores of the catalyst material.

In a preferred embodiment, toluene is alkylated by contacting same with ethylene in the presence of silicalite catalyst materials under reaction conditions which comprise inlet temperatures of from about 350° to about 500° C. These particular temperature conditions have been found to provide improved stability, i.e. retention of activity with time, for the catalysts used in the process. When steam is employed the preferred amount is from about 20,000 to about 60,000 parts per million based on the toluene feed with 40,000 parts per million steam cofeed being especially preferred. The preferred reactant ratios (toluene/ethylene) are from about 7:1 to about 20:1 with the preferred toluene feed WHSV's ranging from about 50 to about 200. Further, operating pressures between about atmospheric and 25 atmospheres can be employed with a range of from about 10 to about 15 being preferred. While a variety of silicalite catalysts materials can be employed, the preferred physical form for the silicalite crystals are those having a crystallite size of less than about 8 microns and Si/Al ratios of at least about 200.

The process of the subject invention can be further exemplified through study of the following examples which are not intended to limit the subject invention in any manner.

EXAMPLES

In each of the examples set forth in Table 1 below toluene is alkylated with ethylene under the reaction conditions specified using a silicalite type catalyst having a particle size of between about 12 and about 20 mesh in a catalyst bed about 8.25 cm deep. The temperatures and pressures indicated in Table I are reactor inlet measurements. In each case the product exiting from the alkylation reactor is analyzed by gas chromotography. The activity of the catalyst material is measured as the percent conversion of ethylene passed through the reactor. Selectivity is determined as a weight percent of ethyltoluene present in the total product weight.

| Example No. | Catalyst* Crys. Size μm; (Si/Al) | Temp. °C. | Pressure PSIG | WHSV (Toluene) | Toluene: Ethylene | Steam, PPM | Cat. Age Hrs. | % Conversion | % Selectivity | Isomer Ratio (P/M/O) |
|---|---|---|---|---|---|---|---|---|---|---|
| 1 | 8 (234) | 474 | 150 | 127 | 17.8 | 40,000 | 24 | 97.9→9.7 | 94.5 | 75.5/22/2.5 |
| 2 | 8 (234) | 462 | 145 | 125 | 17.66 | 40,000 | 24-49 | 89.7→82.3 | 97.1 | 82/16/2 |
| 3 | 8 (234) | 455 | 145 | 126 | 17.6 | 40,000 | 49-71 | 79.4→78.0 | 97.9 | 84.4/13/1.6 |
| 4 | 1-2 | 490 | 150 | 127 | 15.44 | 40,000 | 0-24.5 | 96.7 | 91.6 | 41.42/57.5/1.08 |

-continued

| Example No. | Catalyst* Crys. Size μm; (Si/Al) | Temp. °C. | Pressure PSIG | WHSV (Toluene) | Toluene: Ethylene | Steam, PPM | Cat. Age Hrs. | % Conversion | % Selectivity | Isomer Ratio (P/M/O) |
|---|---|---|---|---|---|---|---|---|---|---|
| 5 | 1-2 (320) | 483 | 151 | 127 | 15.9 | 40,000 | 197-220 | 97.1 | 93.2 | 49.4/50.2/.4 |
| 6 | 1-2 (320) | 486 | 150 | 127 | 15 | 40,000 | 337-346 | 92.1 | 94.4 | 58.1/41.75/0.15 |
| 7 | 1-2 (320) | 486 | 151 | 127 | 15.34 | 40,000 | 26-49 | 97.6 | 93.8 | 46.7/52.9/4 |
| 8 | 1-2 (320) | 450 | 155 | 127 | 15.4 | 40,000 | 52-96 | 100.4 | 96.13 | 50.4/49.4/.2 |
| 9 | 1-2 (320) | 447 | 150 | 127 | 15.98 | 40,000 | 314-321.5 | 97.5 | 96.96 | 59.9/39.9/0.2 |
| 10 | 1-2 (320) | 436 | 152 | 126 | 15.6 | 40,000 | 106-148.5 | 99.5 | 96.7 | 54.4/45.4/.2 |
| 11 | 1-2 (320) | 417 | 150 | 127 | 15.5 | 40,000 | 152-194 | 98.92 | 97.2 | 60.12/39.78/.1 |
| 12 | 1-2 (320) | 394 | 152 | 126 | 15.89 | 40,000 | 223-298 | 88.54 | 97.75 | 73/26.95/.05 |
| 13 | 1-2 (320) | 485 | 155 | 127 | 8.4 | 40,000-80,000 | 326-437 | 88→43 | 95.1 | 68.4/31.4/0.2 ±8 ±8 ±8 |
| 14 | 1-2 (320) | 496 | 155 | 125 | 18.7 | NONE | 0-24 | 97.9 | 88 | 52.9/46.9/0.2 |
| 15 | 1-2 (320) | 494 | 145 | 125 | 18.0 | NONE | 140-161 | 98.9 | 92.2 | 60.8/39.03/0.15 |
| 16 | 1-2 (320) | 473 | 155 | 125 | 18.7 | NONE | 24-48 | 100.5 | 94.3 | 59.3/40.6/0.13 |
| 17 | 1-2 (320) | 455 | 155 | 125 | 18.7 | NONE | 48-72 | 101.7 | 96.3 | 64.6/35.3/0.1 |
| 18 | 1-2 (320) | 437 | 155 | 125 | 18 | NONE | 72-90.5 | 103 | 94.7 | 68.1/31.8/.1 |
| 19 | 1-2 (320) | 425 | 155 | 125 | 18 | NONE | 116-132 | 95.9 | 97.2 | 73.8/26.1/0.1 |
| 20 | 1-2 (320) | 501 | 155 | 126 | 18.3 | NONE | 0-10 | 100.6 | 88.44 | 53.7/45.9/.4 |
| 21 | 1-2 (320) | 453 | 155 | 120 | 11.64 | NONE | 10-70 | 94.8 | 95.1 | 29.5/70.3/.2 |
| 22 | 1-2 (320) | 453 | 155 | 120 | 11.64 | NONE | 10-70 | 94.8 | 95.1 | 46.9/52.9/.16 |
| 23 | 1-2 (320) | 450 | 155 | 129 | 16 | NONE | 0-9 | 83→68 | 91.4 | 65.8/32.8/1.32 |
| 24 | 1-2 (320) | 450-500 | 155 | 64 | 16.1 | 40,000 | 13-72 | 79.9→44.6 | 92.4 | 69.5/29.7/.78 |
| 25 | 1-2 (320) | 492 | 155 | 129 | 15.2 | 40,000 | 0-24 | 94.5 | 88.8 | 60/39.7/.3 |
| 26 | 1-2 (320) | 479 | 155 | 129 | 15.2 | 40,000 | 24-48 | 98.5 | 93.4 | 64.8/34.9/.3 |
| 27 | 1-2 (320) | 465 | 155 | 129 | 15.1 | 40,000 | 48-74 | 101 | 95.3 | 68.2/31.7/.1 |
| 28 | 1-2 (320) | 454 | 155 | 129 | 15.2 | 40,000 | 72-96 | 100 | 96.4 | 71.3/28.5/.2 |
| 29 | 1-2 (320) | 443 | 155 | ? | 15 | 40,000 | 96→121 | 101 | 97.63 | 76.1/23.8/.1 |
| 30 | 1-2 (320) | 492 | 155 | 129 | 15.1 | 40,000 | 121→141 | 98.7 | 94 | 66.9/33/.3 |
| 31 | 1-2 (320) | 458 | 155 | 129 | 7 | NONE | 0→74 | 93.5→22 | 89.4→96.8 | — |
| 32 | >2 (220) | 473 | 155 | 129 | 7 | NONE | 0→82 | 95.03→81 | 89→94.9 | 35.8/60.3/3.9 |
| 33 | 1-2** (320) | 446 | 165 | 130 | 7 | NONE | 0-12 | 89→52 | 92.3→97.6 | 88.45/11.53/0.02 |
| 34 | >1 (220) | 446 | 155 | 130 | 7 | NONE | 0→100 | 98.9→39 | 89.2→95 | 47.2/50.9/1.9 |
| 35 | >1 (220) | 453 | 155 | 130 | 7 | 40,000 | 0→263 | 97.4→58 | 89→96 | 43.3/55.8/0.8 |
| 36 | >1 (220) | 491 | 164 | 130 | 16 | 40,000 | 0→24 | 100.4 | 83.3 | 34.8/67.17/3.03 |
| 37 | >1 (220) | 494 | 163 | 130 | 16 | 40,000 | 124→144 | 94.6 | 91 | 43.39/55.91/.7 |
| 38 | >1 (220) | 487 | 161 | 130 | 16 | 40,000 | 194→216 | 88→87 | 96 | 48.53/50.87/.6 |
| 39 | >1 (220) | 474 | 164 | 130 | 16 | 40,000 | 24→48 | 102 | 90.3 | 39.37/59.69/.98 |
| 40 | >1 (220) | 459 | 164 | 130 | 16 | 40,000 | 48→72 | 103 | 93.3 | 42.87/56.5/.63 |
| 41 | >1 (220) | 457 | 161 | 130 | 16 | 40,000 | 170-192 | 92→87 | 97.6 | 50/49.64/.36 |
| 42 | >1 (220) | 450 | 150 | 130 | 16 | 40,000 | 72-96 | 100 | 93.3 | 45.84/53.59/.57 |
| 43 | >1 (220) | 434 | 163 | 130 | 16 | 40,000 | 96-120 | 104.9 | 94.7 | 48.52/51.14/.34 |

-continued

| Example No. | Catalyst* Crys. Size μm; (Si/Al) | Temp. °C. | Pressure PSIG | WHSV (Toluene) | Toluene: Ethylene | Steam, PPM | Cat. Age Hrs. | % Conversion | % Selectivity | Isomer Ratio (P/M/O) |
|---|---|---|---|---|---|---|---|---|---|---|
| 44 | >1 (220) | 403 | 160 | 130 | 16 | 40,000 | 146-168 | 84→74 | 97.7 | 58.26/41.58/.16 |

*Unless otherwise noted Al₂O₃ binder employed.
**SiO₂ binder

A study of the above data clearly demonstrates that several different silicalite catalysts demonstrate an intrinsic ability to suppress production of ortho isomers of ethyltoluene under a variety of different reaction conditions. The use of a steam cofeed does not affect the ability of the silicalite material to suppress ortho isomer formation and in some instances apparently aids in such suppression. For example, a comparison of Example 34 to Example 35 wherein the same catalyst was used to produce ethyltoluene under essentially the same reaction conditions except for the fact that 40,000 ppm steam cofeed is employed in Example 35, demonstrates that in addition to prolongation of conversion and increased selectivity values, use of the steam also caused the amount of ortho isomer to be halved in comparison to essentially the same conditions without the presence of steam.

One of ordinary skill in the art upon reading the above specification and examples will appreciate that the process of the subject invention can be modified or adapted in a variety of ways. All such modifications or adaptations which fall within the scope of the appended claims are intended to be covered thereby.

We claim:

1. A process for producing dialkyl substituted benzene isomer mixes having less than a thermodynamic equilibrium amount of ortho isomer comprising contacting toluene or ethylbenzene with an alkylating agent under alkylation conditions which do not include steam cofeed in the presence of a crystalline silica polymorph silicalite catalyst and recovering the produced dialkyl benzene isomer mix having an ortho isomer content which is less than the thermodynamic equilibrium amount thereof.

2. The process of claim 1 wherein said alkylation conditions comprise inlet temperatures from about 350° C. to about 500° C.

3. The process of claim 1 wherein toluene is alkylated with ethylene.

4. The process for suppressing production of the ortho isomer during catalytic alkylation of toluene comprising contacting toluene and an alkylating agent under alkylation conditions, which do not include steam cofeed, in the presence of a crystalline silica polymorph silicalite catalyst and recovering the produced alkyl toluene having an ortho isomer content which is less than the thermodynamic equilibrium amount thereof.

5. The process of claim 4 wherein said alkylation conditions comprise inlet temperatures of from about 350° C. to about 500° C.

6. The process of claim 4 wherein said alkylating agent is ethylene.

7. A process for producing an ethyltoluene isomer mix having less than a thermodynamic equilibrium amount of the ortho isomer comprising:
   (a) introducing toluene and ethylene in mole ratios of from about 2 to about 20 into an alkylation zone;
   (b) contacting said toluene and ethylene under alkylation conditions, which do not include steam cofeed, with a crystalline silica polymorph silicalite catalyst; and
   (c) recovering the resulting ethyltoluene isomer mix having an ortho isomer content which is less than the thermodynamic equilibrium amount thereof.

8. The process of claim 1 wherein said catalyst is an unmodified silicalite catalyst.

9. The process of claim 8 in which said ortho isomer is present in a concentration of less than 5 weight percent.

10. The process of claim 4 wherein said catalyst is an unmodified silicalite catalyst.

11. The process of claim 10 in which said ortho isomer is present in a concentration of less than 5 weight percent.

12. The process of claim 7 wherein said catalyst is an unmodified silicalite catalyst.

13. The process of claim 12 wherein said ortho isomer is present in a concentration of less than 5 weight percent.

* * * * *